United States Patent
Medders et al.

(10) Patent No.: US 7,641,156 B2
(45) Date of Patent: Jan. 5, 2010

(54) PORTABLE DRINK STAND

(76) Inventors: Neil Medders, 147 Pika Pl., Alma, GA (US) 31510; Debra Medders, 147 Pika Pl., Alma, GA (US) 31510

( * ) Notice: Subject to any disclaimer, the term of this patent is extended or adjusted under 35 U.S.C. 154(b) by 23 days.

(21) Appl. No.: 12/129,613

(22) Filed: May 29, 2008

(65) Prior Publication Data

US 2009/0294622 A1 Dec. 3, 2009

(51) Int. Cl.
*A47F 5/00* (2006.01)
(52) U.S. Cl. .................. 248/125.8; 248/150; 248/171; 248/230.7; 211/85; 211/203
(58) Field of Classification Search .............. 248/122.1, 248/121, 125.8, 125.9, 146, 150, 151, 157, 248/161, 166, 188.6, 230.7, 231.81, 170, 248/171; 108/50.12, 128, 150; 135/16, 19, 135/98; 211/71.01, 85, 195, 203
See application file for complete search history.

(56) References Cited

U.S. PATENT DOCUMENTS

| | | | | |
|---|---|---|---|---|
| 554,661 A * | 2/1896 | Doolittle | ..................... | 108/105 |
| 721,425 A * | 2/1903 | Clyde | ......................... | 248/170 |
| 1,409,609 A * | 3/1922 | Stockle | ........................ | 135/96 |
| 3,076,557 A * | 2/1963 | Husted et al. | ............... | 211/196 |
| 3,464,664 A * | 9/1969 | Nugent | ........................ | 248/435 |
| 3,757,705 A * | 9/1973 | Maslow | ................. | 108/147.13 |
| 4,828,211 A | 5/1989 | McConnell | | |
| 5,483,901 A | 1/1996 | Tisbo | | |
| 5,647,075 A * | 7/1997 | Perkins | ........................... | 5/127 |
| 5,715,954 A * | 2/1998 | Zaremba | ..................... | 211/107 |
| 5,873,312 A * | 2/1999 | Mauro-Vetter | ......... | 108/147.21 |
| 5,934,634 A * | 8/1999 | Lindblom | ................ | 248/230.1 |
| 5,970,536 A * | 10/1999 | Suarez | .......................... | 4/599 |
| 6,766,912 B1 * | 7/2004 | Gibbs | .......................... | 211/74 |
| 6,971,613 B2 * | 12/2005 | Shendelman | ................ | 248/150 |
| 7,311,289 B2 | 12/2007 | Mori | | |
| 2005/0040297 A1 | 2/2005 | Saraf | | |

* cited by examiner

*Primary Examiner*—Korie H. Chan
(74) *Attorney, Agent, or Firm*—John D. Tran; Buus, Kim, Kuo & Tran, APC

(57) ABSTRACT

The present invention is a portable stand that generally comprises of an upper telescopic pipe, a lower telescopic pipe that is movably inserted into the upper telescopic pipe to form a longitudinal shaft, a plurality of expandable legs at the bottom of the longitudinal shaft with a leaf spring mechanism, a round plate holder, a bottle holder, a v-shaped plate holder, a flower vase, umbrella stand, a box for magnetic compass or LED light, a knickknack pouch and a beverage holder. The longitudinal shaft of the portable stand is adjusted for a desired height. A controller knob is slid up and down, to fold and expand the expandable legs at the bottom of the longitudinal shaft to a desired angle. Various attachments are attached onto the longitudinal shaft depending on the need.

9 Claims, 10 Drawing Sheets

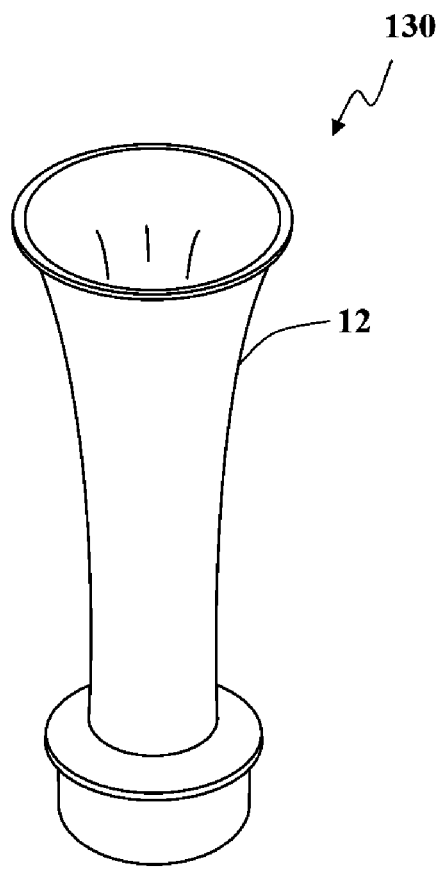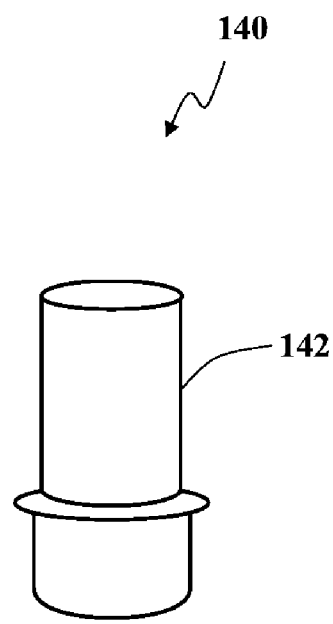
Fig. 13
Fig. 14
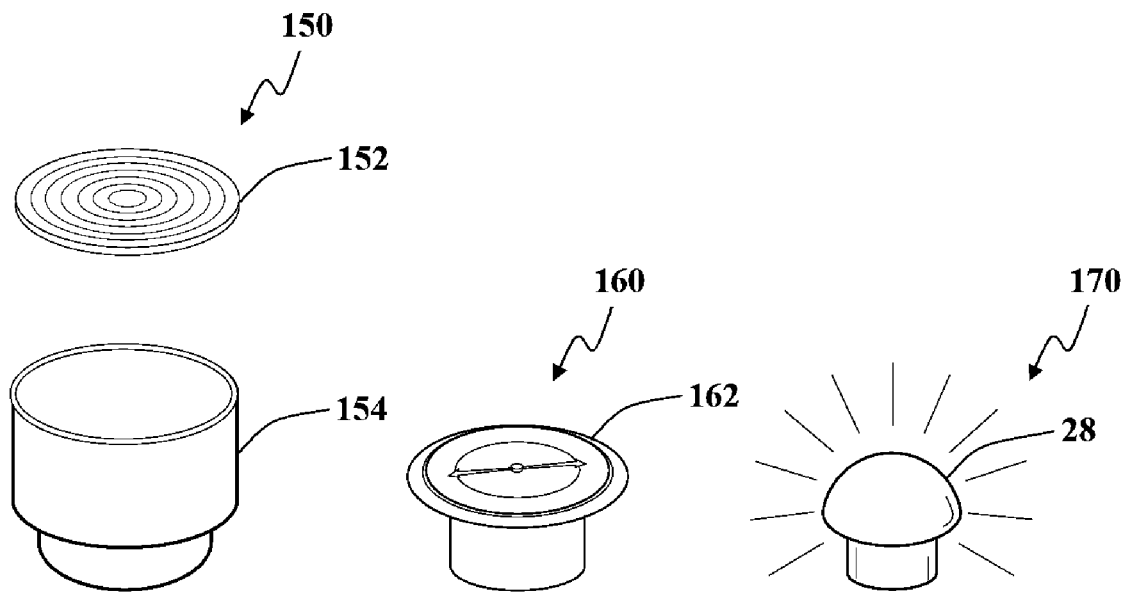
Fig. 15
Fig. 16
Fig. 17

PORTABLE DRINK STAND

BACKGROUND OF THE INVENTION (1) Field of the Invention

This invention relates to multi purpose stands, and more particularly to a portable and foldable drink stand with various attachments that can be snapped on the stand as required.

(2) Description of Related Art

Foldable stands have been an economical solution for different indoor and outdoor occasions such as performances, meetings, conferences, and especially for camping trips. A foldable stand can be folded into compact packets during transportation and provides greater maneuverability and stability while traveling. The greatest advantage with foldable stands is that they offer flexible space management in small areas. They are lightweight, easy to stack and carry. Foldable stands in varying sizes and shapes are available in aluminum or plastic. U.S. Pat. No. 20050040297 to Saraf on Feb. 24, 2005 explains a multi-purpose ground stand used to securely affix an umbrella or any like device. The device is fixed into any malleable surface such as sand, grass, gravel or dirt and the device is intended to accommodate any size or shape of commercially available beach or sun umbrellas. These stands have been intended to use for only umbrellas and limited to outdoor applications where they must be pushed in to the ground to achieve stability. This approach does not allow for use of the product on hard surfaces.

U.S. Pat. No. 5,483,901 to Tisbo on Jan. 16, 1996 relates to a tray table of modular construction with readily replaceable and interchangeable plastic molded components that can be assembled by hand. A pair of first legs and second legs is connected to the underside of the tray. Such a tray table is suitable for use in leveled surfaces and not suitable for use in sloped terrain due to its design constraints.

Similarly, U.S. Pat. No. 4,828,211 to Mc Connell on May 9, 1989 teaches a foldable support for beverage container which can be quickly folded, assembled, disassembled, and adjusted to accommodate containers of a variety of sizes. Such bottle or glass holders are generally limited to very specific purposes. Moreover, these bottle or glass holders do not have the flexibility to hold many glasses at the same time. This bottle or glass holders do not have the ability to function at many different heights.

In order to avoid the above problems, U.S. Pat. No. 7,311,289 to Mori on Dec. 25, 2007, discloses a multi-purpose foldable stand that is simple in structure and capable of using on a table and when not in use, the stand is folded into a compact size for storage. The stand has two identical U-shaped frames. Each of the frames includes a horizontal leg portion, an upright support portion, and a horizontal arm portion, to which spring clips or hooks are attached for suspending articles. Such a multi-purpose foldable stand is assigned themselves to indoor and decorative uses and not for outdoor practical usage. Usually, these devices which accomplish its goal are typically difficult for storage or for disassembling the parts.

While many of the prior art designs provide a certain basic amount of stability, each of these stands is quite limited since it is designed to support the item for which it was specifically designed. Furthermore, most all of these traditional stand designs cannot be set up on ground that is not planar and level and in most-every case, traditional stand designs are suitable for supporting a single article.

All referenced patents, applications and literatures are incorporated herein by reference to their entirety. Furthermore, where a definition or use of a term in a reference, which is incorporated by reference herein is inconsistent or contrary to the definition of that term provided herein, the definition of that term provided herein applies and the definition of the term in the reference does not apply. The invention may seek to satisfy one or more of the above-mentioned desire. Although the present invention may obviate one or more of the above-mentioned desires, it should be understood that some aspects of the invention might not necessarily obviate them.

In these respects, the portable stand according to the present invention substantially departs from the conventional concepts and designs of the prior art, and so doing provides a portable stand that is not anticipated, rendered obvious, suggested, or even implied by any of the prior art portable drink stand, either alone or in combination thereof

BRIEF SUMMARY OF THE INVENTION

In view of the foregoing disadvantages inherent in the known types of portable stand and means now present in the prior art, the general purpose of the present invention, which will be described subsequently in greater detail, is to provide a portable stand on which various accessories are mounted depending upon the use.

Another object of the present invention is to provide a portable stand, which is compact and foldable;

Another object of the present invention is to provide a portable stand, which can be adjusted for varying degrees of height and a rotate lock prevents further movement of the portable stand;

Another object of the present invention is to provide a portable stand, which can be folded into a pointed shovel like base for unleveled terrain or spread out to stand on normal level surfaces;

Another object of the present invention is to provide a portable stand, which is comprised of expandable legs with a leaf spring mechanism for folding and unfolding the expandable leg assembly;

Another object of the present invention is to provide a portable stand, which is user-friendly and allows for an all in one device;

Another object of the present invention is to provide a portable drink stand which can house multiple attachments which can hold a variety of items such as plates, drinks, wine glasses, utensils, napkins, wireless phones, keys, books and similar reading materials and other miscellaneous items;

To attain this, the present invention in one embodiment generally comprises of a portable stand having an upper telescopic pipe, a lower telescopic pipe that is movably inserted into the upper telescopic pipe to form a longitudinal shaft and a plurality of expandable legs at the bottom of the longitudinal shaft. The portable stand has various attachments that include a round plate holder, a bottle holder, a v-shaped plate holder, a flower vase on the top of the drink stand, a knickknack pouch and a beverage holder.

In typical use, the longitudinal shaft of the portable stand is adjusted for a desired height. The rotate lock prevents further movement of the longitudinal shaft. A controller knob with a slot in the lower telescopic pipe is slid up and down, to fold and expand the expandable legs at the bottom of the longitudinal shaft to a desired angle.

A round plate holder, flower vase, umbrella stand, and a box for magnetic compass or LED light can be attached on the top of the longitudinal shaft as required. A v-shaped plate holder, beverage holder and a knickknack pouch can be attached on an elastic grip that passes through the upper telescopic pipe. A bottle holder is attached onto a second sleeve that is inserted and tightened onto the upper telescopic pipe.

There has thus been outlined, rather broadly, the more important features of the invention in order that the detailed description thereof may be better understood, and in order that the present contribution to the art may be better appreciated. There are additional features of the invention that will be described hereinafter.

In this respect, before explaining at least one embodiment of the invention in detail, it is to be understood that the invention is not limited in its application to the details of the construction and to the arrangements of the components set forth in the following description or illustrated in the drawings. The invention is capable of other embodiments and of being practiced and carried out in various ways. Also, it is to be understood that the phraseology and terminology employed herein are for the purpose of the description and should not be regarded as limiting. To accomplish the above and related objects, this invention may be embodied in the form illustrated in the accompanying drawings, attention being called to the fact, however, that the drawings are illustrative only, and that changes may be made in the specific construction illustrated.

BRIEF DESCRIPTION OF THE DRAWING(S)

Various other objects, features and attendant advantages of the present invention will become fully appreciated as the same becomes better understood when considered in conjunction with the accompanying drawings, in which like reference characters designate the same or similar parts throughout the several views, and wherein:

FIG. 13 is a perspective view of a flower vase;

FIG. 14 is a perspective view of an umbrella stand;

FIG. 15 is a perspective view of a box for magnetic compass or LED light;

FIG. 16 is a perspective view of a magnetic compass;

FIG. 17 is a perspective view of an LED light;

DETAILED DESCRIPTION OF THE INVENTION

The invention and its various embodiments can now be better understood by turning to the following detailed description of the preferred embodiments, which are presented as illustrated examples of the invention defined in the claims. It is expressly understood that the invention as defined by the claims may be broader than the illustrated embodiments described below.

Many alterations and modifications may be made by those having ordinary skill in the art without departing from the spirit and scope of the invention. Therefore, it must be understood that the illustrated embodiment has been set forth only for the purposes of example and that it should not be taken as limiting the invention as defined by the following claims. For example, notwithstanding the fact that the elements of a claims are set forth below in a certain combination, it must be expressly understood that the invention includes other combinations of fewer, more or different elements, which are disclosed herein even when not initially claimed in such combinations.

Figure 1:
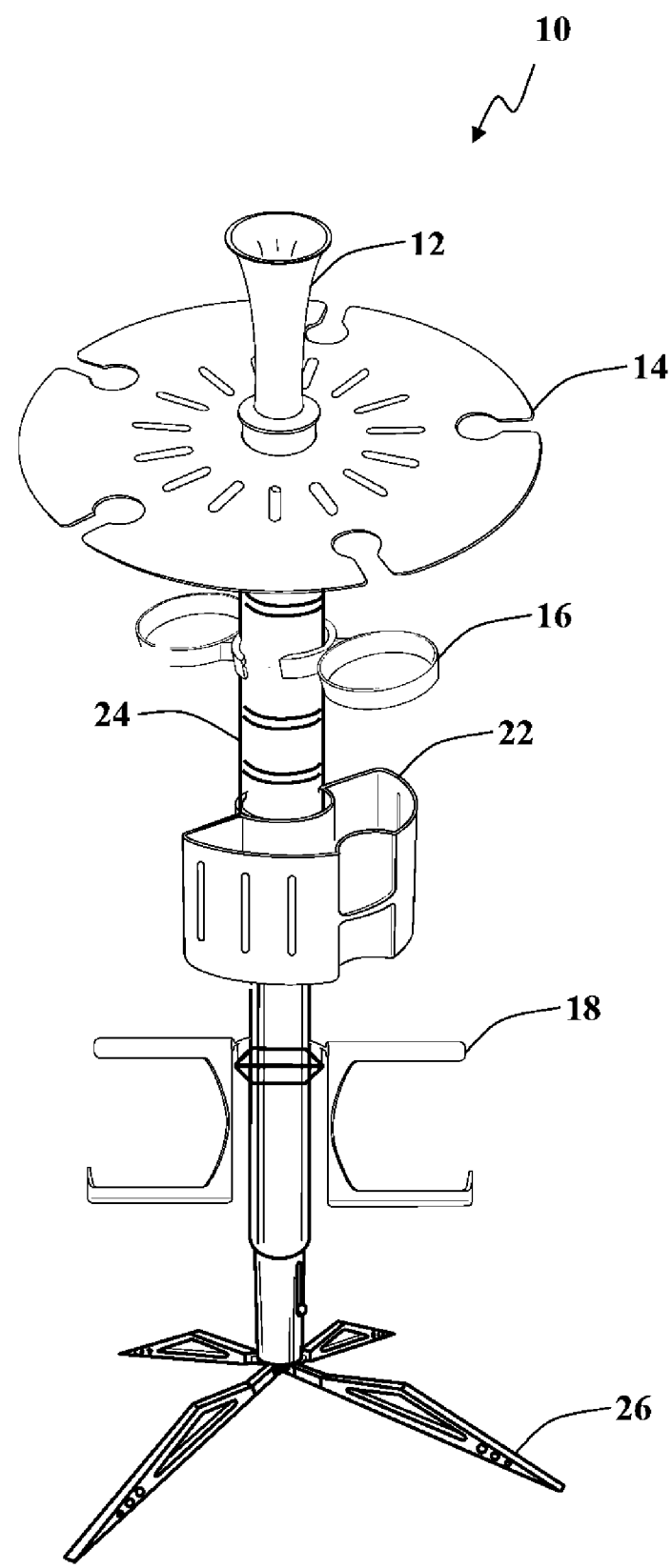
FIG. 1 is a perspective view of a portable stand in accordance with the present invention.

Referring now to the drawings, which are provided by way of illustration and example, and wherein like reference numerals designate like or corresponding elements among the several views, there is shown in FIG. 1, the portable stand 10 having an upper telescopic pipe 214, a lower telescopic pipe 216 that is movably inserted into the upper telescopic pipe 214 to form a longitudinal shaft 32 and a plurality of expandable legs 26 at the bottom of the longitudinal shaft 32. The portable stand 10 has various attachments that include a round plate holder 14 that holds food plates, a bottle holder 18 that holds drink bottles, a v-shaped plate holder 72 that holds food plates, a flower vase 12 on the top of the portable stand 10, a knickknack pouch 22 that holds miscellaneous products and a beverage holder 16 that holds drinks safely. A first sleeve and a second sleeve (not pictured) are inserted into the upper telescopic pipe 214 and tightened using screws to stop further movement of the sleeves.

Figure 2:
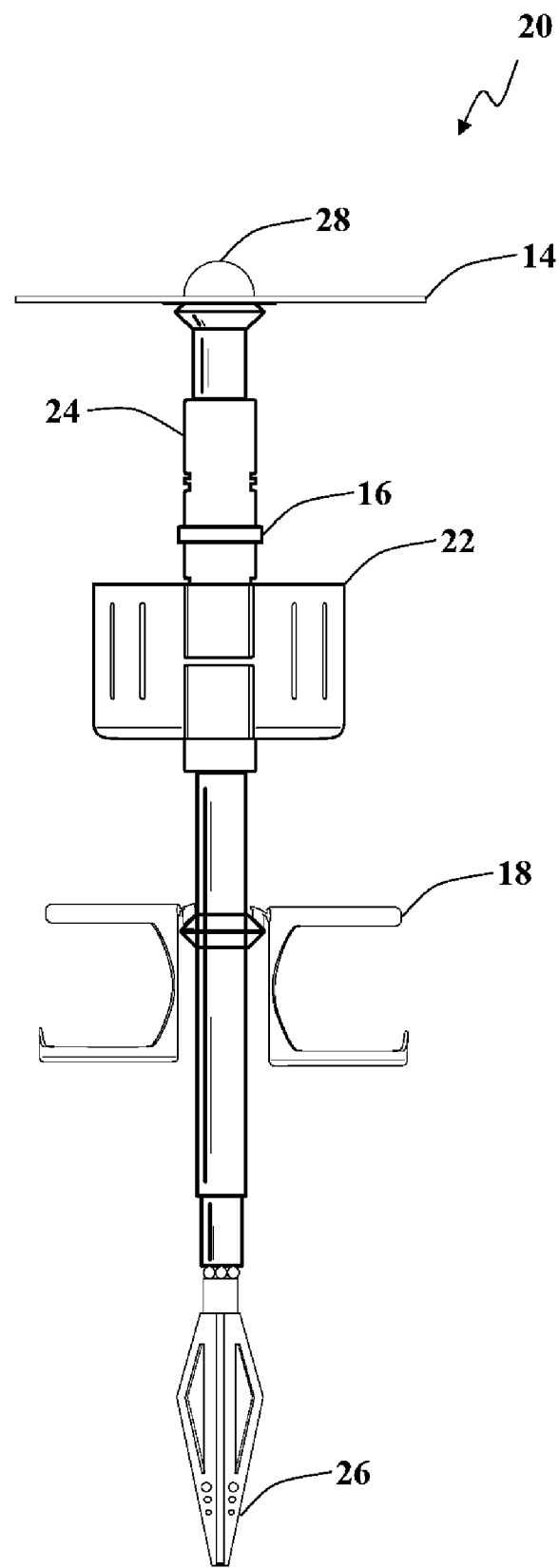
FIG. 2 is a side view of a portable stand.

Turning now to the embodiment of FIG. 2, the portable stand 20 can fold into a pointed shovel like base to be punched into an unleveled terrain or it can spread out to stand on normal level surfaces.

Figure 3:
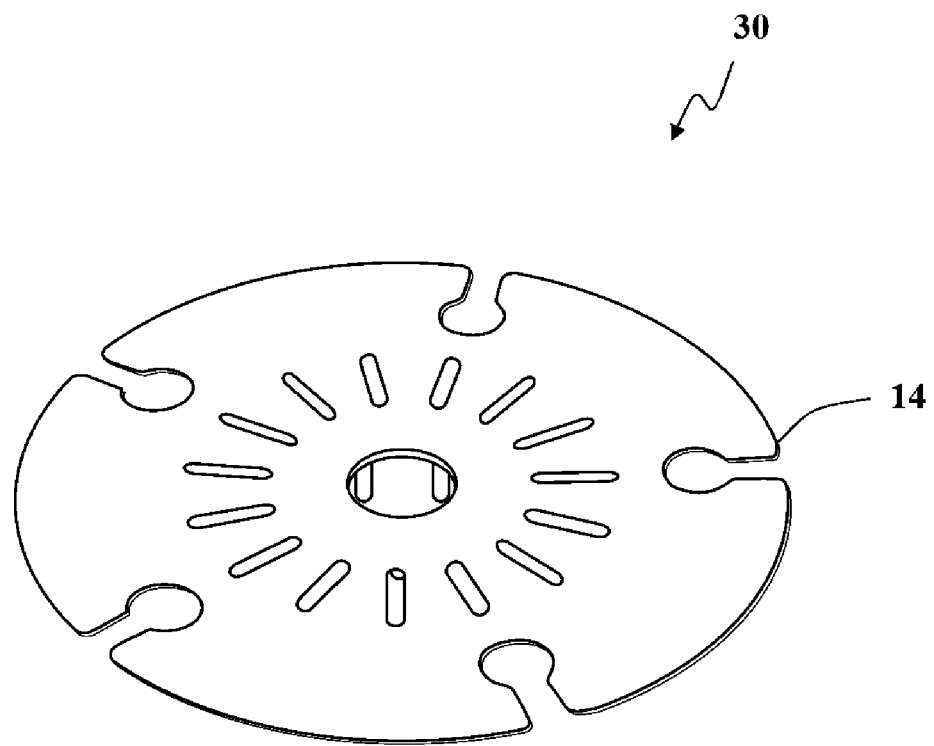
FIG. 3 is a perspective view of a round plate holder.
Figure 4:
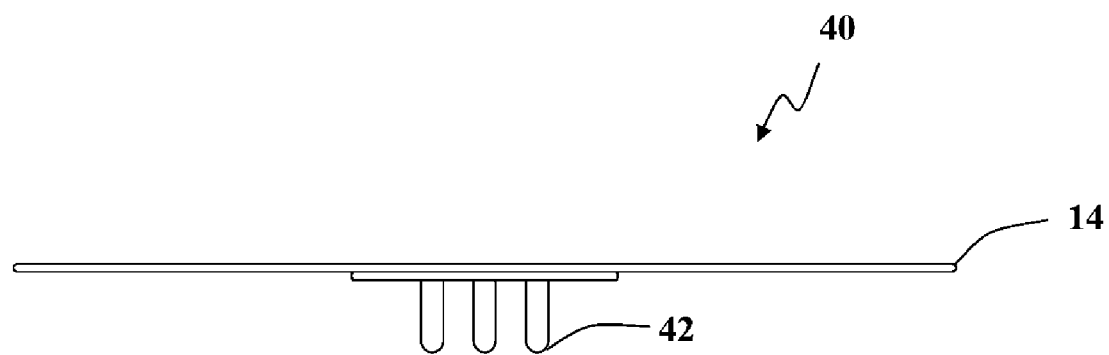
FIG. 4 is a front view of a round plate holder.
Figure 5:
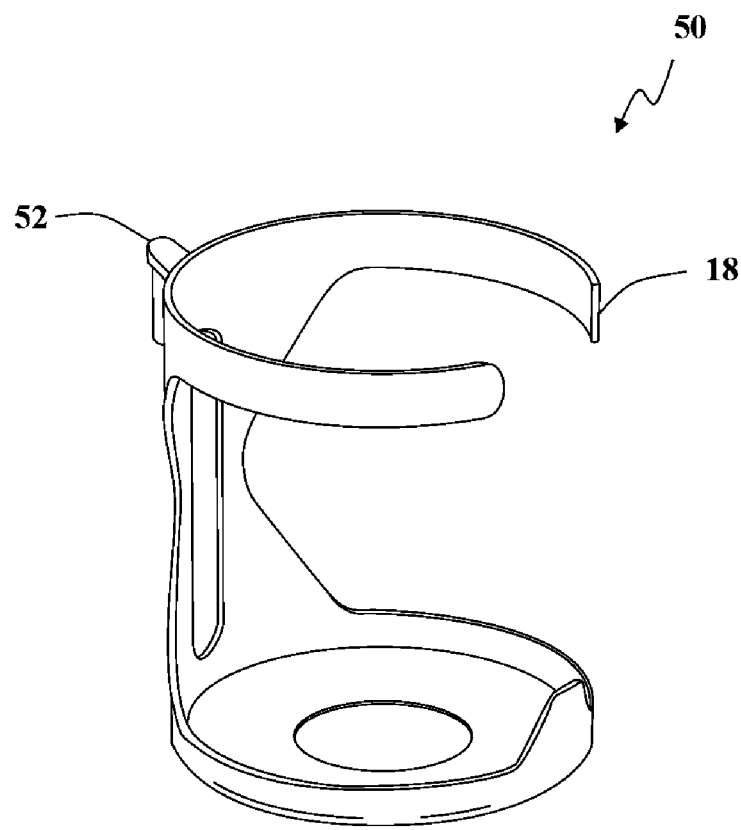
FIG. 5 is a perspective view of a bottle holder.
Figure 6:
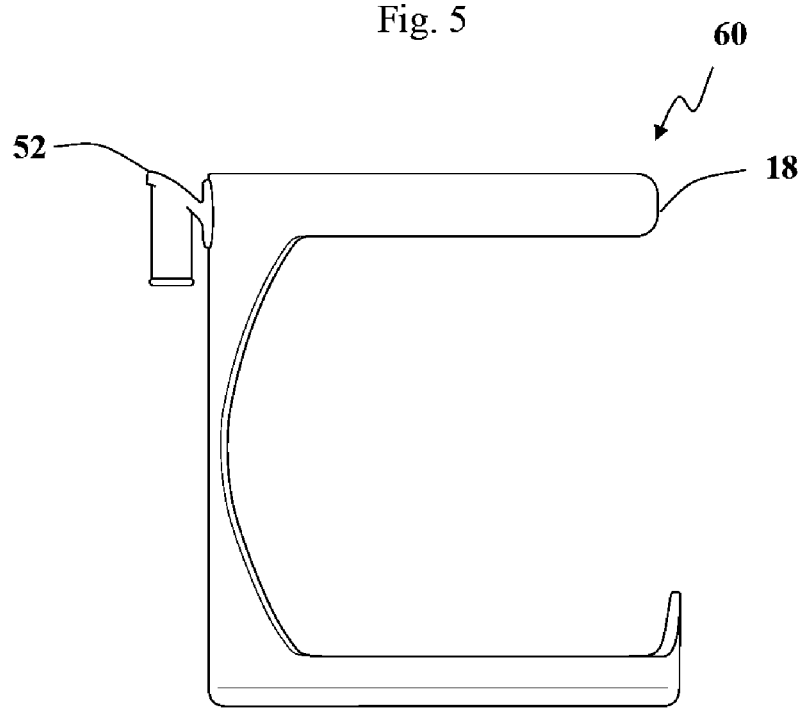
FIG. 6 is a side view of a bottle holder.

FIG. 3 shows a perspective view of a round plate holder 14 that holds food plates. As shown in FIG. 4, the round plate holder 14 has a plurality of elongations 42 that is inserted and secured onto an top ring 212. FIG. 5 shows a bottle holder 18 that holds drink bottles with an elongation 52 on the top. FIG. 6 shows a bottle holder 18, where the elongation 52 on the top of the bottle holder 18 can be inserted onto a second sleeve (not pictured) that is inserted and tightened onto the upper telescopic pipe 214.

Figure 7:
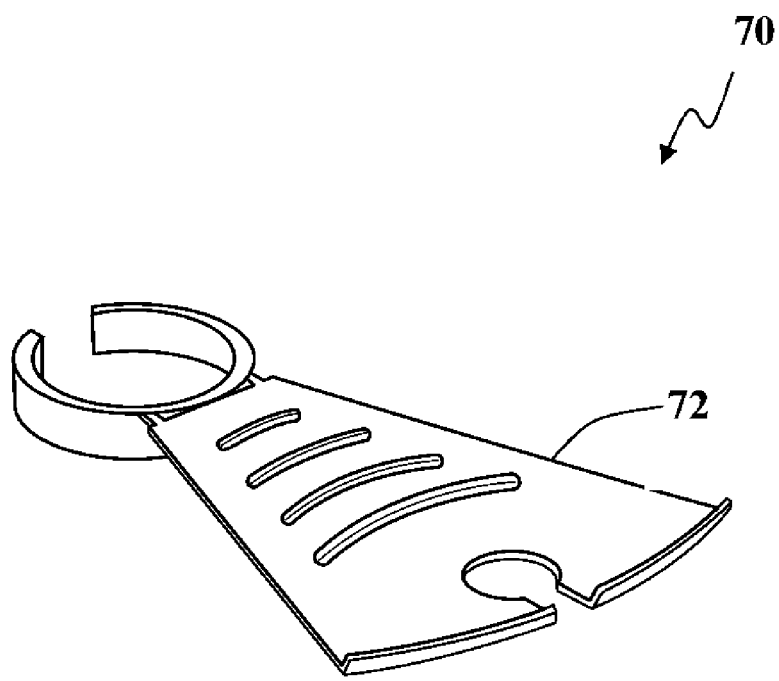
FIG. 7 is a perspective view of a v-shaped plate holder.
Figure 8:
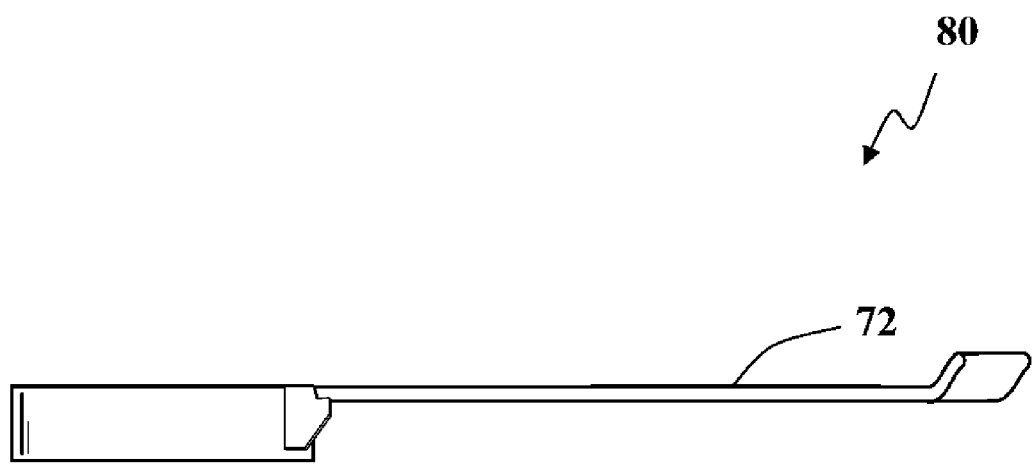
FIG. 8 is a side view of a v-shaped plate holder.
Figure 9:
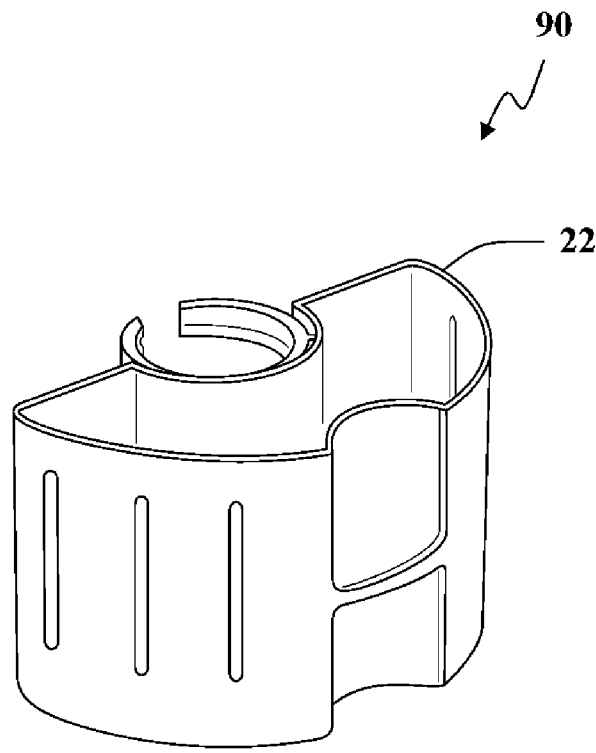
FIG. 9 is a perspective view of a knickknack pouch.
Figure 10:
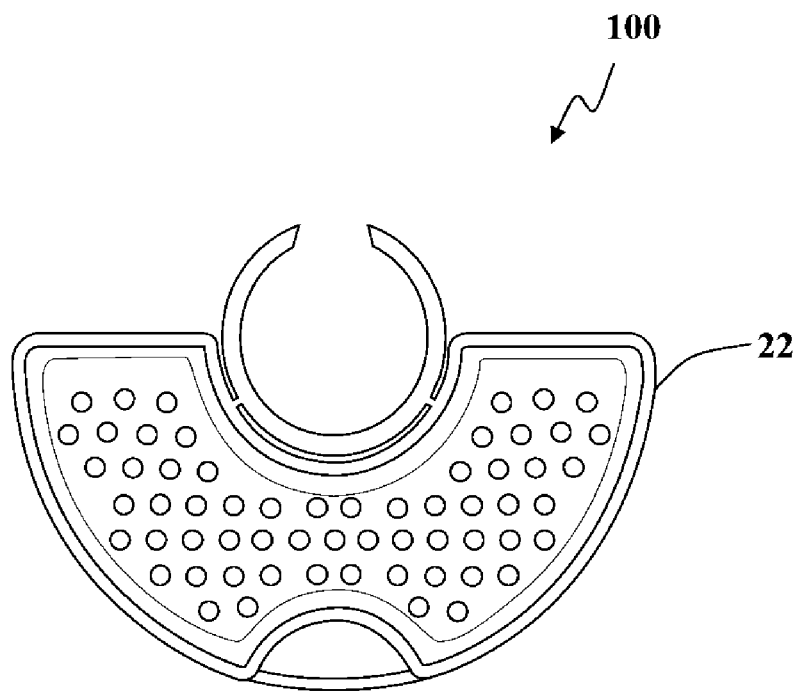
FIG. 10 is a top view of a knickknack pouch.
Figure 11:
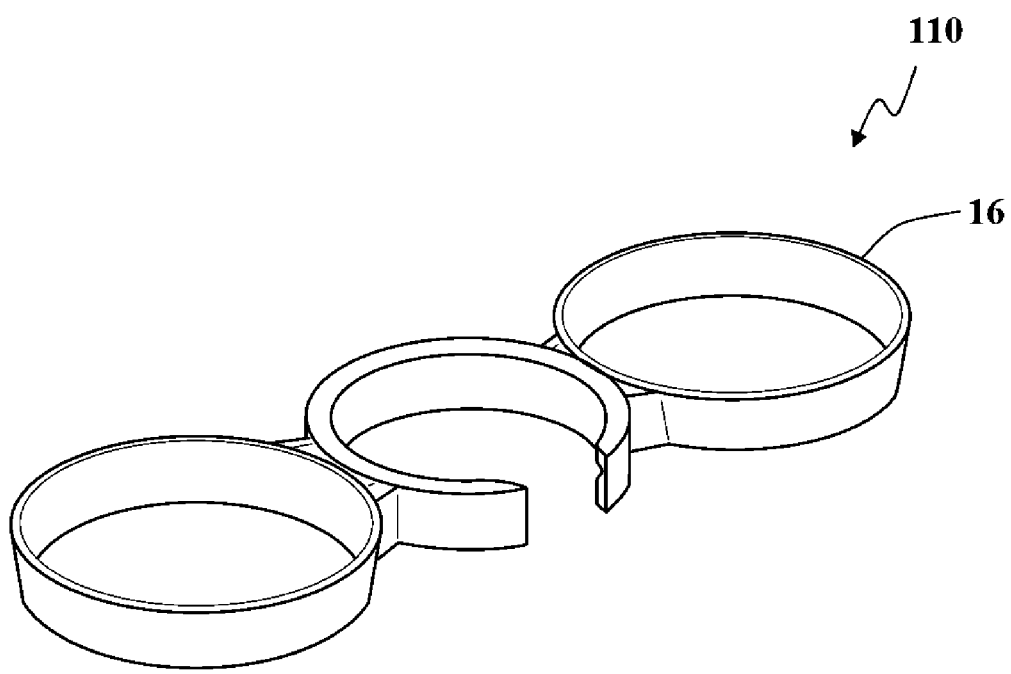
FIG. 11 is a perspective view of a beverage holder.
Figure 12:
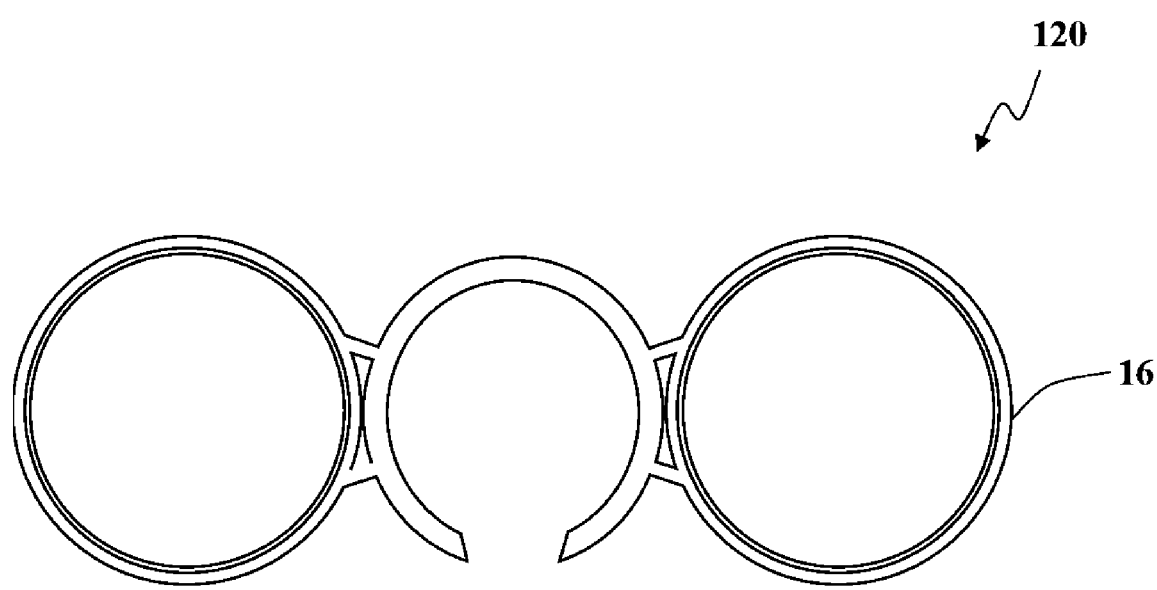
FIG. 12 is a top view of a beverage holder.

FIG. 7 shows a v-shaped plate holder 72 that holds food plates. FIG. 8 shows the side view of the v-shaped plate holder 72, which can be attached on an elastic grip 24 passing through the upper telescopic pipe 214. FIG. 9 shows a knickknack pouch 22 that holds miscellaneous products. FIG. 10 shows a top view of the knickknack pouch 22, which can be attached on an elastic grip 24 passing through the upper telescopic pipe 214. FIG. 11 shows a beverage holder 16 that holds drink safely. FIG. 12 shows a top view of the beverage holder 16 which can be attached on an elastic grip 24 passing through the upper telescopic pipe 214. The elastic grip 24 with clamp grooves is made of polymer.

FIG. 13, FIG. 14 and FIG. 15 shows a flower vase 12, an umbrella stand 142 and a box 154 with a transparent lid 152 respectively. At least one of a flower vase 12, an umbrella stand 142 and a box 154 with a transparent lid 152 can be attached on the top of the longitudinal shaft 32 as required. FIG. 16 and FIG. 17 shows a magnetic compass 162 and an LED light 28 respectively. At least one of a magnetic compass 162 and an LED light 28 can be placed inside the box 154.

Figure 18:
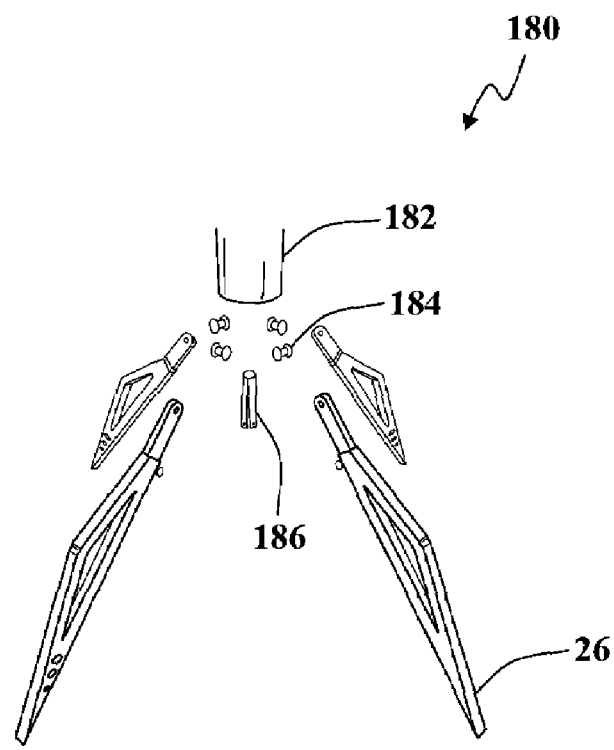
FIG. 18 is an exploded view of an expandable leg assembly.
Figure 19:
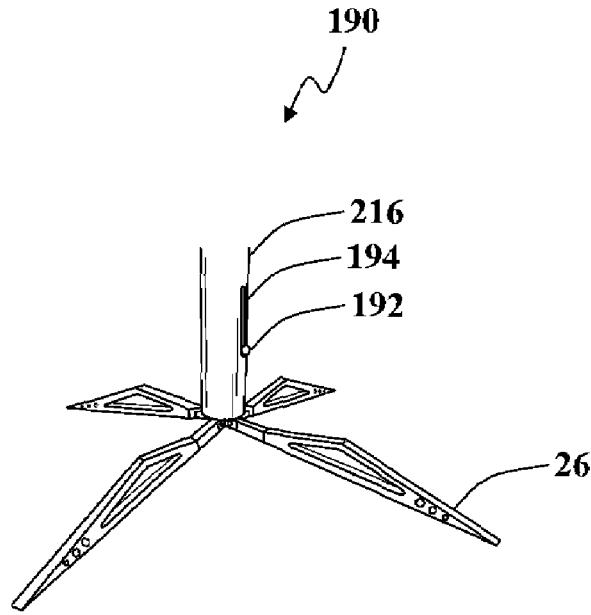
FIG. 19 is a perspective close view of a plurality of expandable legs in spread out position.
Figure 20:
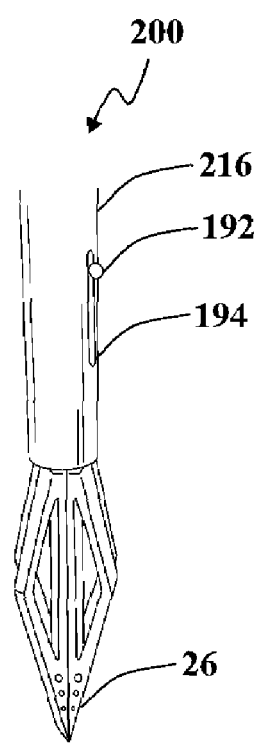
FIG. 20 is a perspective close view of a plurality of expandable legs in folded position.

FIG. 18 shows an expandable leg assembly 180 at the bottom of the longitudinal shaft 32. The expandable leg assembly 180 has a lower stand member joint 1 (not pictured) in which lower stand friction angles (not pictured) and lower stand members 26 are fastened using screws (not pictured) and rivets 184 respectively. A spring 186 is positioned in the lower stand member joint 2 182 using rivets 184. FIG. 19 shows a plurality of expandable legs 26 in spread out position where the controller knob 192 is in down position. The expandable legs 26 are provided with a leaf spring mechanism wherein the controller knob 192 is provided with a slot 194 in the lower telescopic pipe 216. The controller knob 192 is slid up and down to fold and expand the expandable legs 26 to a desired angle respectively. FIG. 20 shows a plurality of expandable legs 26 in folded position where the controller knob 192 is in upper position.

Figure 21:
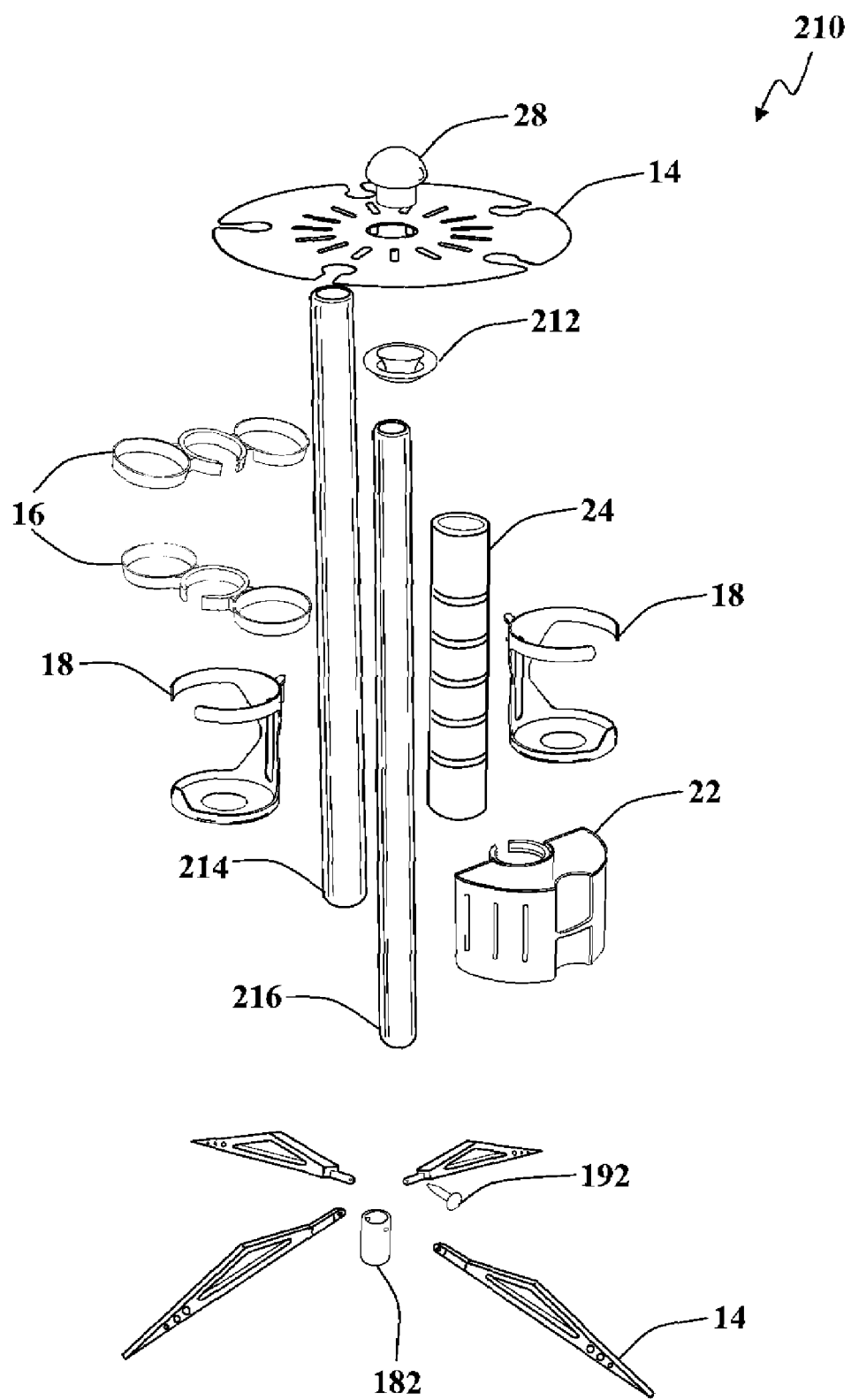
FIG. 21 is an exploded view of a portable stand.

FIG. 21 shows an exploded view of the portable stand 10 where the attachments are attached onto the longitudinal shaft 32 as required. A rotate lock (not pictured) is provided on the upper telescopic pipe 214 to prevent the telescopic movement after adjusting it at a desired height. There is a provision for storing the folded portable stand 10 in a bag (not pictured). The portable stand 10 is compact, foldable and can be used on any terrain and for any scenario.

Thus, specific embodiments and applications of the portable stand have been disclosed. It should be apparent, however, to those skilled in the art that many more modifications besides those already described are possible without departing from the inventive concepts herein. The inventive subject matter, therefore, is not to be restricted except in the spirit of the appended claims. Moreover, in interpreting both the specification and the claims, all terms should be interpreted in the broadest possible manner consistent with the context. In particular, the terms "comprises" and "comprising" should be interpreted as referring to elements, components, or steps in a non-exclusive manner, indicating that the referenced elements, components or steps may be present, or utilized, or combined with other elements, components, or steps that are not expressly referenced. Where the specification claims refer to at least one of something selected from the group consisting of A, B, C . . . and N, the text should be interpreted as requiring only one element from the group, not A plus N, or B plus N, etc.

What is claimed is:

1. A portable stand for various accessories, comprising:
    an upper telescopic pipe;
    a lower telescopic pipe that is movably inserted into the upper telescopic pipe to form a longitudinal shaft; and
    a plurality of expandable legs coupled to the lower telescopic pipe wherein the lower telescopic pipe having a slot and a controller knob, wherein the controller knob coupled to the expandable legs and the controller knob slides along the slot to adjust the expandable legs for use;
    wherein each of the expandable legs is in triangular shape with at least one aperture to relieve stress acted upon,
    wherein when the controller knob is slid upward along the slot, the expandable legs are folded and a side of each of the expandable legs align to form a spearhead having a pointed end,
    whereby a plurality of attachments are coupled to the longitudinal shaft for holding various accessories.

2. The portable stand device as recited in claim 1, wherein at least one of a flower vase, umbrella stand, and a box for magnetic compass or LED light is attached on the top of the longitudinal shaft.

3. The portable stand device as recited in claim 1, wherein a round plate holder is fixed on a top ring that is attached on the top of the longitudinal shaft.

4. The portable stand device as recited in claim 1, wherein a v-shaped plate holder, beverage holder and knickknack pouch are attached on an elastic grip passing through the upper telescopic pipe.

5. The portable stand device as recited in claim 1, wherein a round plate holder, a bottle holder, a v-shaped plate holder, a flower vase, a knickknack pouch and a beverage holder are attached onto the longitudinal shaft.

6. The portable stand device as recited in claim 4, wherein the elastic grip with clamp grooves is made of polymer.

7. The portable stand device as recited in claim 1, wherein the device is compact and foldable.

8. The portable stand device as recited in claim 1, wherein the expandable legs having a length disposed from a proximal end to a distal end of the expandable legs and no more than one half of the length is retractable into the lower telescopic pipe.

9. The portable stand device as recited in claim 1, wherein the spearhead having a circumference and a diameter of the circumference of the spearhead is wider than a diameter of the lower telescopic pipe.

\* \* \* \* \*